(12) United States Patent
Louderback

(10) Patent No.: US 6,255,066 B1
(45) Date of Patent: Jul. 3, 2001

US006255066B1

(54) BACTERIAL VAGINOSIS SCREENING TECHNIQUE AND A DIAGNOSTIC KIT FOR USE THEREIN

(76) Inventor: Allan L. Louderback, P.O. Box 761, Temple City, CA (US) 91780

( * ) Notice: Subject to any disclaimer, the term of this patent is extended or adjusted under 35 U.S.C. 154(b) by 0 days.

(21) Appl. No.: 09/499,802

(22) Filed: Feb. 8, 2000

(51) Int. Cl.$^7$ ................................ C12Q 1/04; C12Q 1/00
(52) U.S. Cl. .................... 435/34; 435/4; 436/111
(58) Field of Search ........................... 435/34, 4; 436/111

(56) References Cited

U.S. PATENT DOCUMENTS

| | | |
|---|---|---|
| 3,119,751 | 1/1964 | Chaney . |
| 5,124,254 | 6/1992 | Hewlins et al. . |
| 5,660,790 | 8/1997 | Lawrence et al. . |
| 5,827,200 | 10/1998 | Caillouette . |
| 5,853,767 * | 12/1998 | Melman ............................... 424/659 |
| 5,910,447 * | 6/1999 | Lawrence et al. .................... 436/111 |

FOREIGN PATENT DOCUMENTS 2199944   7/1988   (GB) .

OTHER PUBLICATIONS

Berthelot, Repertoire de Chemie Applique, 1, 284 (1859).
Fawcett et al, J. Clin. Path., vol. 13:156–159 (1960).
Chaney et al, Clinical Chemistry 8(2);130–132 (1962).
Horn et al, Clinica Chemica Acta, vol. 17:99–103, (1967).
Digecon, Model 1011, Direction Insert for the Determination of Blood Urea Nitrogen in Serum or Heparinized Plasma, Sherwood Med. Ind., St. Louis, MO, circa 1972.
Henry, R. et al, Clinical Chemistry, 2nd Edition, p. 521, Harper & Row, Hagerstown, MD (1974).
H.J. Conn Biological Stains, 9th Edition, pp. 372–375 (1977) The Williams and Wilkins Co, Baltimore, MD.
UN–Test, Direction insert, Hyland, Div. Travenol Laboratories, Los Angeles, CA (Jun., 1977).
The Merck Index, 10th Edition, p. 445–446 (1983), Rahway, NJ.
Tietz, N., Fundamentals of Clinical Chemistry, 3rd Edition, p. 677, W.B. Saunders Company, Philadelphia, PA (1987).
Spinillo et al, Early Human Dev., 48(1–2):81–91 (1997).
Dammann et al, Develop. Med. of Child Neurology, 39:836–840 (1997).
The Vaginitis Report, vol. One, 3M National Vaginitis Assoc., St. Paul, MN (1998).
The Vaginitis Report, vol. Two, 3M National Vaginitis Assoc., St. Paul, MN (1998).
The Vaginitis Report, vol. Three, 3M National Vaginitis Assoc., St. Paul, MN (1998).
3M National Vaginitis Assoc. News and Information, Press Release, pp. 1–10 (1998).

* cited by examiner

*Primary Examiner*—Louise N. Leary

(57) ABSTRACT

A screening test for bacterial vaginosis is performed by (a) combining a sample of vaginal fluid with a developer reagent selected from the group consisting of phenol, derivatives thereof, and mixtures thereof to form a first reaction medium; (b) combining the first reaction medium with a water soluble base and a halogen-containing oxidizing agent to form a second reaction medium having a pH of at least about 9.5; and (c) observing the color of the second reaction medium. The concentration of the halogen-containing oxidizing agent in the second reaction medium is about 0.12 or greater (on a molar basis) than the concentration of the developer reagent in the second reaction medium. The foregoing procedure can be used to test for the presence of amines in any aqueous fluid as well as for synthesizing various dyes.

47 Claims, No Drawings

BACTERIAL VAGINOSIS SCREENING TECHNIQUE AND A DIAGNOSTIC KIT FOR USE THEREIN

FIELD OF THE INVENTION

The invention pertains to a method for screening for bacterial vaginosis and a diagnostic kit for use therein. More generically, the invention pertains to a method for detecting the presence of an amine in a sample of fluid, a diagnostic kit for use therein, as well as a method for making a dye, especially 2,6-dichloroindophenol.

BACKGROUND OF THE INVENTION

Vaginitis is the most common gynecological problem in adult women. Infectious vaginitis presents itself in three primary forms: (a) bacterial vaginosis, (b) candidal vaginitis or "yeast", and (c) trichomonas vaginitis or "trich." Bacterial vaginosis, which affects up to 25% of American women in the normal clinical populations, is nearly twice as common as Candida and is, in fact, the most common form of vaginal infection. Bacterial vaginosis is caused by a replacement of the normal vaginal flora with facultative anaerobic bacteria, primarily *Gardnerella vaginalis*. Unfortunately, the symptoms of bacterial vaginosis are non-specific or non-existent and differential diagnosis is problematic.

Complications associated with bacterial vaginosis represent a major health care cost burden. For example, obstetric complications of bacterial vaginosis include (1) preterm labor/birth, (2) low birth weight babies; (3) premature rupture of the amniotic membranes or PROM; (4) amniotic fluid infections; (5) postpartum endometritis, and (6) chorioamnionitis. Preterm/low birth weight babies is the second leading cause of infant mortality, next to birth defects. Also, bacterial vaginosis is suspected of being one of the many causes of cerebral palsy. In addition, gynecologic complications of bacterial vaginosis include (1) postoperative infections; (2) pelvic inflammatory disease (PID); (3) abnormal cervical cytology, (4) increased susceptibility to sexually transmitted diseases (STDs), and (5) posthysterectomy infections. STDs such as chlamydia, herpes, syphillis, gonorrhea, and trichomoniasis also cause potential harm to the fetus. Furthermore, a Swedish study reported in *Acta Obstetricia et Gynecologica Scandinavica*, 73:586–588 (1994) suggests that bacterial vaginosis may potentially be a cofactor with human papilloma virus in the development of cervical intraepithelial neoplasia (CIN), a precursor of cervical cancer.

While the rapid, accurate diagnosis of bacterial vaginosis is critical to an effective treatment decision and can minimize serious complications and costs, recent studies show that many women with bacterial vaginosis incorrectly self-diagnose their symptoms, mistaking them for yeast infections. The consensus among experts today is that proper differential diagnosis of vaginitis is essential for any OB/GYN practice, and that routine screening for bacterial vaginosis may become increasingly appropriate. Northern Europe has already implemented this approach and now conducts bacterial vaginosis tests in conjunction with annual Pap smears. Furthermore, since self-obtained vaginal swabs have been shown to be reliable specimens for use in the diagnosis of bacterial vaginosis, experts agree that home diagnostics may be the wave of the future.

SUMMARY OF THE INVENTION

One embodiment of the present invention is a screening technique for bacterial vaginosis that can be used at home or in a doctor's office. The bacterial vaginosis screening technique is directed to detecting the presence of one or more amines (e.g., putrescine (a.k.a. 1,4-diaminobutane or tetramethylenediamine) and cadaverine (a.k.a. 1,5-diaminopentane) which are known to occur at significantly elevated levels in Gardnerella-related vaginitis) in a sample of vaginal fluid and comprises the steps of (a) combining the sample of vaginal fluid with phenol (or any developer reagent selected from the group consisting of phenol, derivatives thereof, and mixtures thereof) to form a first reaction medium; (b) combining the first reaction medium with sodium hydroxide and/or potassium hydroxide (or any other water soluble base) and sodium hypochlorite (or any other halogen-containing oxidizing agent) to form a second reaction medium having a pH of at least about 9.5; and (c) observing the color of the second reaction medium (preferably to determine the presence of a 2,6-dichloroindophenol salt), where the concentration of the halogen-containing oxidizing agent in the second reaction medium is about 0.12 or greater (on a molar basis) than the concentration of the developer reagent in the second reaction medium. If the screening technique detects the presence of amines, the patient should be seen by a physician or at a clinic to have a microbial culture of her vaginal fluid grown out to determine the exact source of the amine-producing organism in order for a physician to prescribe an appropriate treatment plan.

A second and broader embodiment of the invention encompasses employing the foregoing method to detect the presence of an amine in any sample of fluid.

A third embodiment of the invention is a diagnostic kit suitable for use in the above described procedures. The diagnostic kit comprises (a) the developer reagent; (b) the water soluble base; and (c) the halogen-containing oxidizing agent, where (i) the concentration of the halogen-containing oxidizing agent in a reaction medium formed by combining the developer reagent, the water soluble base, and the halogen-containing oxidizing agent is about 0.12 or greater (on a molar basis) than the concentration of the developer reagent in the reaction medium and (ii) the pH of the reaction medium is at least about 9.5.

In a fourth and broader embodiment, the invention encompasses a method for preparing a dye which comprises the steps of: (a) reacting the developer reagent with an amine to form a first reaction medium; and (b) combining the first reaction medium with the water soluble base and the halogen-containing oxidizing agent to form a second reaction medium having a pH of at least about 9.5, where the concentration of the halogen-containing oxidizing agent in the second reaction medium is about 0.12 or greater (on a molar basis) than the concentration of the developer reagent in the second reaction medium.

The above-summarized embodiments of the invention as well other embodiments thereof are described in more detail below.

DETAILED DESCRIPTION OF THE INVENTION

One method for screening for the presence of bacterial vaginosis in accordance with the present invention entails taking a sample of vaginal fluid. This can be accomplished, for example, by a vaginal swab. The sample of vaginal fluid is then contacted with a developer reagent to form a first reaction medium. The first reaction medium is next combined with a solution comprising a water soluble base and a halogen-containing oxidizing agent to form a second reaction medium, which typically has a pH of at least about 9.5. After a period of time (such as after a lapse of about 5 to 10 minutes) the color of the second reaction medium is observed. Alternatively, the sample vaginal fluid can be initially combined with a solution that comprises the developer reagent, the water soluble base, and the halogen-containing oxidizing agent or the sample of vaginal fluid can be first mixed with developer reagent and then mixed sequentially with the water soluble base and the halogen-containing oxidizing agent in any desired order.

The developer reagent employed in the bacterial vaginosis screening technique is generally selected from the group consisting of phenol, phenol derivatives (e.g., 2-phenylphenol, 3-phenylphenol, 4-phenylphenol), and mixtures of thereof. Phenol is the preferred developer reagent.

The amount of developer reagent employed in the methodology of the present invention should be sufficient to react with enough of any amine present in the sample to obtain a positive result. Generally, the developer reagent is used in an amount such that the concentration of the developer reagent present in a reaction medium formed by combining the sample of fluid, the developer reagent, the water soluble base, and the halogen-containing oxidizing agent (and prior to any reaction) is at least about 0.1 M, more commonly, at least about 0.2 M, even more commonly at least about 0.3 M, and most commonly at least about 0.4 M. (To avoid tedious lists of every possible number and every possible subrange within a stated range, all numbers and all subranges within each stated range are incorporated herein by reference.) In fact, the developer reagent can be present in the reaction medium up to its solubility limit.

The water soluble base employed in the bacterial vaginosis screening methodology of the present invention is usually an alkali metal salt typically selected from the group consisting of alkali metal hydroxides (e.g., sodium hydroxide and potassium hydroxide), alkali metal carbonates (e.g., sodium carbonate and potassium carbonate), trialkali metal phosphates (e.g., trisodium phosphate and tripotassium phosphate), and mixtures thereof. Preferably, the water soluble base is sodium hydroxide and/or potassium hydroxide, with sodium hydroxide being the most preferred.

The water soluble base is employed in amount such that the pH of a reaction medium formed by combining the sample of vaginal fluid, the developer reagent, the water soluble base, and the halogen-containing oxidizing agent is usually at least about 9.5, more commonly at least about 10, even more commonly at least about 10.5, and most commonly at about 11. Preferably, the water soluble base is present in a concentration sufficient for the pH of the reaction medium to be at least about 11.25, more preferably at least about 11.5, even more preferably at least about 11.75, and most preferably at least about 12, 12.25, 12.5, and also 12.75.

Sodium hypochlorite, trichloroisocyanuric acid, 1-bromo-3-chloro-5-dimethylhydantoin are common halogen-containing oxidizing agents that can be used in the bacterial vaginosis screening technique of the present invention. (Chlorine, bromine, and iodine are the halogens typically present in the halogen-containing oxidizing agents.) The preferred halogen-containing oxidizing agent is sodium hypochlorite.

The concentration of the halogen-containing oxidizing agent in the reaction medium (prior to any reaction) is typically about 0.12 or greater (on a molar basis) than the concentration of the developer reagent in the reaction medium. More typically, the concentration of the halogen-containing oxidizing agent in the reaction medium is about 0.13, 0.14, 0.15, 0.16, 0.17, 0.18, 0.19 or greater (on a molar basis) than the concentration of the developer reagent in the reaction medium. Preferably, the concentration of the halogen-containing oxidizing agent in the reaction medium is about 0.20, more preferably about 0.21, and most preferably about 0.22 or greater (on a molar basis) than the concentration of the developer reagent in the reaction medium. While the concentration of the halogen-containing oxidizing agent in the reaction medium can be as high as the solubility limit of the halogen-containing oxidizing agent in the reaction medium, on a practical basis the halogen-containing oxidizing agent in the reaction medium is commonly less than about 1 times the concentration of the developer reagent in the reaction medium (on a molar basis). More commonly, the concentration of the halogen-containing oxidizing agent in the reaction medium is less than about 0.9, 0.8, 0.7, 0.6, 0.5, 0.4, or even 0.3 times the concentration of the developer reagent in the reaction medium (on a molar basis).

The following Table I exemplifies diagnostic kits for use in the methodology of the present invention for the specific case where the reagents are formulated as two solution, namely, a first solution containing just the developer reagent (e.g., phenol) and a second solution containing the water soluble base (e.g., sodium hydroxide) and the halogen-containing oxidizing agent (e.g., sodium hypochlorite).

TABLE I

Exemplary Diagnostic Kits Comprising Two Solutions

| Diagnostic Kit | 2-Component Reagent | | Developer Reagent |
|---|---|---|---|
| | Sodium Hydroxide, $M^a$ | Sodium Hypocholorite, $M^a$ | Phenol, $M^a$ |
| 1 | 1.875 | 0.084 | 0.5 |
| 2 | 2.500 | 0.114 | 0.5 |
| 3 | 3.125 | 0.142 | 0.5 |
| 4 | 3.750 | 0.170 | 0.5 |
| 5 | 4.375 | 0.199 | 0.5 |

TABLE I-continued

Exemplary Diagnostic Kits Comprising Two Solutions

| Diagnostic Kit | 2-Component Reagent | | Developer Reagent |
|---|---|---|---|
| | Sodium Hydroxide, M[a] | Sodium Hypocholorite, M[a] | Phenol, M[a] |
| 6 | 5.000 | 0.227 | 0.5 |
| 7 | 0.625 | 0.114 | 0.5 |
| 8 | 1.250 | 0.114 | 0.5 |
| 9 | 1.875 | 0.114 | 0.5 |
| 10 | 2.500 | 0.028 | 0.5 |
| 11 | 2.500 | 0.056 | 0.5 |
| 12 | 2.500 | 0.084 | 0.5 |
| 13 | 0.313 | 0.114 | 0.5 |
| 14 | 0.156 | 0.114 | 0.5 |
| 15 | 0.625 | 0.114 | 0.5 |
| 16 | 2.500 | 0.114 | 0.25 |
| 17 | 0.313 | 0.114 | 0.25 |
| 18 | 0.156 | 0.114 | 0.25 |

[a]"M" denotes Molar (moles per liter).

A significant safety aspect of the present invention is that immersion of the vaginal swab into the developer solution followed the addition of the water soluble base and halogen-containing oxidizing agent results in the inactivation of fungi, bacteria, and viruses that may be present in the vaginal sample on the swab. Accordingly, the swab can be safely disposed of without fear of contamination.

While other compositions can be present in the diagnostic kit or screening methodology of the present invention, generally they are not. For example, nitroprusside can be present in the developer solution, but typically is not.

EXAMPLES

The following examples are intended to further illustrate (and not limit) the invention.

Examples 1–20

Determination of Operable Molar Concentrations for Solutions Comprising Sodium Hydroxide and Sodium Hypochlorite Introduction:

A set of solutions comprising various concentrations of both sodium hydroxide and sodium hypochlorite and a set of solution comprising various concentrations of phenol were prepared and tested for efficacy.

Reagents:

A. Phenol Reagent

Phenol reagents were prepared by dissolving various amounts of phenol in about 100 ml of deionized water. A description of each of the prepared phenol solutions is set forth below in Table A.

TABLE A

Composition of Phenol Reagents

| Phenol Reagent | Phenol | | Water |
|---|---|---|---|
| | gm | M[a] | ml |
| 1 | 5 | 0.5 | 100 |
| 2 | 2.5 | 0.25 | 100 |

[a]"M" denotes Molar (moles per liter).

B. 2-Component Reagent

Various amounts of sodium hydroxide and sodium hypochlorite were added to 100 ml of deionized water. The sodium hypochlorite employed was liquid bleach (i.e., a solution of 5.25% sodium hypochlorite). A description of each of the prepared two-component solutions is set forth in the following Table B.

TABLE B

Composition of Two-Component Reagents

| 2-Component Reagent | Sodium Hydroxide | | | Sodium Hypocholorite | | | | Water |
|---|---|---|---|---|---|---|---|---|
| | gm | M[a] | X·MR1[b] | ml[c] | gm | M[a] | Y·MR1[d] | ml |
| 1 | 2.5 | 0.625 | 1 | 4.0 | 0.21 | 0.028 | 1 | 100 |
| 2 | 5.0 | 1.250 | 2 | 8.0 | 0.42 | 0.056 | 2 | 100 |
| 3 | 7.5 | 1.875 | 3 | 12.0 | 0.63 | 0.084 | 3 | 100 |
| 4 | 10.0 | 2.500 | 4 | 16.0 | 0.84 | 0.114 | 4 | 100 |
| 5 | 12.5 | 3.125 | 5 | 20.0 | 1.05 | 0.142 | 5 | 100 |
| 6 | 15.0 | 3.750 | 6 | 24.0 | 1.26 | 0.170 | 6 | 100 |
| 7 | 17.5 | 4.375 | 7 | 28.0 | 1.47 | 0.199 | 7 | 100 |
| 8 | 20.0 | 5.000 | 8 | 32.0 | 1.68 | 0.227 | 8 | 100 |
| 9 | 2.5 | 0.625 | 1 | 16.0 | 0.84 | 0.114 | 4 | 100 |
| 10 | 5.0 | 1.250 | 2 | 16.0 | 0.84 | 0.114 | 4 | 100 |
| 11 | 7.5 | 1.875 | 3 | 16.0 | 0.84 | 0.114 | 4 | 100 |
| 12 | 10.0 | 2.500 | 4 | 4.0 | 0.21 | 0.028 | 1 | 100 |

TABLE B-continued

Composition of Two-Component Reagents

| 2-Component Reagent | Sodium Hydroxide | | | Sodium Hypocholorite | | | | Water |
|---|---|---|---|---|---|---|---|---|
| | gm | M[a] | X•MR1[b] | ml[c] | gm | M[a] | Y•MR1[d] | ml |
| 13 | 10.0 | 2.500 | 4 | 8.0 | 0.42 | 0.056 | 2 | 100 |
| 14 | 10.0 | 2.500 | 4 | 12.0 | 0.63 | 0.084 | 3 | 100 |
| 15 | 1.25 | 0.313 | ½ | 16.0 | 0.84 | 0.114 | 4 | 100 |
| 16 | 0.63 | 0.156 | ¼ | 16.0 | 0.84 | 0.114 | 4 | 100 |
| 17 | 0 | 0 | 0 | 16.0 | 0.84 | 0.114 | 4 | 100 |

[a]. "M" denotes Molar (moles per liter).
[b]. "X•MR1" means times the molar concentration of sodium hydroxide employed in 2-component reagent 1.
[c]. Sodium hypochlorite added as a 5.25% solution (i.e., added in the form of bleach).
[d]. "Y•MR1" means times the molar concentration of sodium hypochlorite employed in 2-component reagent 1.

Test Protocol and Results:

In each test, about 100 μL of a putrescine solution (about 150 mg/dL) was added to a test tube. Then about 250 μL of a phenol solution was added with mixing to form a first reaction mixture or medium. Finally, about 250 μL of a 2-component solution comprising sodium hydroxide and sodium hypochlorite was added to the first reaction mixture to form a second reaction mixture. A timer was then started and the color of the second reaction mixture was observed after a lapse of about 5 to about 6 minutes. The results are noted below in Table C.

sodium hypochlorite is necessary to achieve a visible color for a positive sample. Furthermore, the tests demonstrate that the concentration of the phenol reagent can be varied while obtaining a color for an amine-containing sample.

Examples 21–26

Determination of pH of 2-Component Reagent and of the Reaction Medium

The pH of about 3 to about 5 mL of various 2-component reagent solutions was taken and the results are set forth below in Table D.

TABLE C

Summary of Test Results

| | Two-Component Reagent | | | |
|---|---|---|---|---|
| Example | Sodium Hydroxide X · MR1[a] | Sodium Hypocholorite Y · MR1[b] | Phenol Reagent M[c] | Observations |
| 1 | 1 | 1 | 0.5 | No color visually observed. |
| 2 | 2 | 2 | 0.5 | No color visually observed. |
| 3 | 3 | 3 | 0.5 | Mild blue color observed. |
| 4 | 4 | 4 | 0.5 | Strong royal blue color observed. |
| 5 | 5 | 5 | 0.5 | Strong royal blue color observed. |
| 6 | 6 | 6 | 0.5 | Strong royal blue color observed. |
| 7 | 7 | 7 | 0.5 | Strong royal blue color observed. |
| 8 | 8 | 8 | 0.5 | Strong royal blue color observed. |
| 9 | 1 | 4 | 0.5 | Strong royal blue color observed. |
| 10 | 2 | 4 | 0.5 | Strong royal blue color observed. |
| 11 | 3 | 4 | 0.5 | Strong royal blue color observed. |
| 12 | 4 | 1 | 0.5 | Slight blue tinge observed. |
| 13 | 4 | 2 | 0.5 | Blue tinge stronger than Ex. 12. |
| 14 | 4 | 3 | 0.5 | Blue tinge stronger than Ex. 13. |
| 15 | ½ | 4 | 0.5 | Steely blue/gray color observed.[d] |
| 16 | ¼ | 4 | 0.5 | Steely gray color observed.[e] |
| 17 | 0 | 4 | 0.5 | No color observed. |
| 18 | 1 | 4 | 0.25 | Light blue color observed. |
| 19 | ½ | 4 | 0.25 | Light blue color observed. |
| 20 | ¼ | 4 | 0.25 | Slight color observed. |

[a]"X · MR1" means times the molar concentration of sodium hydroxide employed in 2-component reagent 1.
[b]"Y · MR1" means times the molar concentration of sodium hypochlorite employed in 2-component reagent 1.
[c]"M" denotes Molar (moles per liter).
[d]After being allowed to settle overnight, the second reaction mixture exhibited a blue color and a black precipitate was at the bottom of the tube.
[e]After being allowed to settle overnight, the second reaction mixture exhibited a light blue color and a black precipitate was at the bottom of the tube.

Conclusions:

The above tests indicate that some sodium hydroxide is necessary. (Compare for instance Examples 9–11 and 15–17.) In addition, the tests show that a threshold level of

TABLE D pH of Various Two-Component Reagents

| Example | Two-Component Reagent | | pH |
|---|---|---|---|
| | Sodium Hydroxide X · MR1[a] | Sodium Hypocholorite Y · MR1[b] | |
| 21 | 1 | 4 | 13.55 |
| 22 | ½ | 4 | 13.25 |
| 23 | ¼ | 4 | 12.04 |

[a] "X · MR1" means times the molar concentration of sodium hydroxide employed in 2-component reagent 1.
[b] "Y · MR1" means times the molar concentration of sodium hypochlorite employed in 2-component reagent 1.

Next, various reaction mediums were formed by combining about 1.2 mL of a putrescine solution (150 mg/dL), about 3 mL of a 0.5 M phenol reagent solution, and about 3 ml of different two-component reagent solutions. After a period of about 6 minutes after forming the reaction mixtures, the pH of each of the reaction mixtures was taken and the results are shown in the following Table E.

TABLE E pH of Various Reaction Mixtures

| Example | Two-Component Reagent | | Phenol Reagent M[c] | pH |
|---|---|---|---|---|
| | Sodium Hydroxide X · MR1[a] | Sodium Hypocholorite Y · MR1[b] | | |
| 24 | 1 | 4 | 0.5 | 12.88 |
| 25 | ½ | 4 | 0.5 | 10.33 |
| 26 | ¼ | 4 | 0.5 | 9.86 |

[a] "X · MR1" means times the molar concentration of sodium hydroxide employed in 2-component reagent 1.
[b] "Y · MR1" means times the molar concentration of sodium hypochlorite employed in 2-component reagent 1.
[c] "M" denotes Molar (moles per liter).

While above Table C indicates that all the reagent combinations examined in Examples 24–26 of the foregoing Table E are operable, nevertheless the data set forth in Table C shows that it is preferred for the pH of the reaction medium to be about 10.5 or greater.

Examples 27–30

Determination of Color Intensity as a Function of Putrescine Concentration in Test Samples Reagents:

Three reagent solutions containing various concentrations of putrescine were prepared and their compositions are set forth below in Table F.

TABLE F

Composition of Putrescine Solutions

| Reagent | Putrescine, mg | Deionized Water, mL |
|---|---|---|
| 1 | 0 | 100 |
| 2 | 12 | 100 |
| 3 | 50 | 100 |
| 4 | 150 | 100 |

Test Protocol:

The test procedure described above with respect to Examples 1–20 was employed using the phenol and 2-component solutions listed in the following Table G.

TABLE G

Results of Testing Solutions having Various Putrescine Concentrations

| Example | Two-Component Reagent | | Phenol Reagent M[c] | Putrescine Reagent mg/dL | Observations |
|---|---|---|---|---|---|
| | Sodium Hydroxide X · MR1[a] | Sodium Hypocholorite Y · MR1[b] | | | |
| 27 | 4 | 4 | 0.5 | 0 | No color observed. |
| 28 | 4 | 4 | 0.5 | 12 | Weak blue color observed. |
| 29 | 4 | 4 | 0.5 | 50 | Blue color observed. |
| 30 | 4 | 4 | 0.5 | 50 | Strong royal blue color observed. |

[a] "X · MR1" means times the molar concentration of sodium hydroxide employed in 2-component reagent 1.
[b] "Y · MR1" means times the molar concentration of sodium hypochlorite employed in 2-component reagent 1.
[c] "M" denotes Molar (moles per liter).

Examples 31–34

2,6-dichloroindophenol Confirmation Tests

To each of the final solutions formed in above Examples 27–30 was added tiny drops of 6N hydrochloric acid and mixed to form a first solution. The color of each of the resulting first solutions was observed. Next, a small amount of ascorbic acid powder was added to each test tube containing the first solutions and mixed again to form a second solution. The color of each of the second solutions was then observed. The results are set forth in Table H below.

TABLE H

Results of 2,6-dichloroindophenol Confirmation Tests

Two-Component Reagent

| Example | Sodium Hydroxide X · MR1[a] | Sodium Hypocholorite Y · MR1[b] | Phenol Reagent M[c] | Putrescine Reagent mg/dL | Observations |
|---|---|---|---|---|---|
| 31 | 4 | 4 | 0.5 | 0 | No color change observed. |
| 32 | 4 | 4 | 0.5 | 12 | Blue to red (reddish) to colorless. |
| 33 | 4 | 4 | 0.5 | 50 | Blue to red (reddish) to colorless. |
| 34 | 4 | 4 | 0.5 | 150 | Blue to red (reddish) to colorless. |

[a]"X · MR1" means times the molar concentration of sodium hydroxide employed in 2-component reagent 1.
[b]"Y · MR1" means times the molar concentration of sodium hypochlorite employed in 2-component reagent 1.
[c]"M" denotes Molar (moles per liter).

The change of color from blue to red to colorless in Examples 31–34 confirms the dye present in these solutions is 2,6-dichloroindophenol as described in the Merck Index (10th edition), page 352, Merck & Co., Rahway, N.J. (1983) (hereinafter referred to as the "Merck Index"). (The reader may wish to note that in several diagnostic assays a blue color is developed where the dye produced is indophenol (a.k.a. indophenol blue). If indophenol-containing solutions are subjected to the above described Merck Index test, the color change observed is from the initial blue to brown and back to blue. This confirms that 2,6-dichloroindophenol is structurally different from indophenol.)

Examples 35–38

Assay Using a Phenol Derivative

A 5% solution of 2-phenylphenol was prepared by dissolving 5 gm of 2-phenylphenol in 100 mL of deionized water.

The test procedure described above with respect to Examples 1–20 was employed using the 5% solution of 2-phenylphenol and the 2-component solution listed below in Table I.

TABLE I

Results of Tests Employing a 5% 2-Phenylphenol Reagent Solution

Two-Component Reagent

| Example | Sodium Hydroxide X · MR1[a] | Sodium Hypocholorite Y · MR1[b] | Phenol Reagent M[c] | Putrescine Reagent mg/dL | Observations |
|---|---|---|---|---|---|
| 35 | 4 | 4 | 0.5 | 0 | No color observed. |
| 36 | 4 | 4 | 0.5 | 12 | Weak green color observed. |
| 37 | 4 | 4 | 0.5 | 50 | Green color observed. |
| 38 | 4 | 4 | 0.5 | 150 | Dark green color observed. |

[a]"X · MR1" means times the molar concentration of sodium hydroxide employed in 2-component reagent 1.
[b]"Y · MR1" means times the molar concentration of sodium hypochlorite employed in 2-component reagent 1.
[c]"M" denotes Molar (moles per liter).

Example 39

Assay Using A Bromo- and Chloro-Containing Oxidizing Agent

A 5% solution of phenol was prepared by dissolving 5 gm of phenol in 100 mL of deionized water.

A 2-component solution was prepared by dissolving 10 gm of sodium hydroxide and 2 gm of 1-bromo-3-chloro-5-dimethylhydantoin in 100 mL of deionized water.

The test procedure described above with respect to Examples 1–20 was employed using the 5% phenol solution and the 2-component solution prepared above and a blue color was observed. Further, the Merck Index test showed blue to red to colorless, thereby confirming that the synthesized dye was 2,6-dihologenated indophenol.

Example 40

System of Invention does not React with Ammonia to Give a Color

An ammonium sulfate solution (about 20 mg/dL ammonium nitrogen) was added to the 0.5 M phenol reagent and mixed to form a first reaction medium. Then, to the first reaction medium was added a 2-component reagent solution comprising about 2.5 M sodium hydroxide and 0.114 M sodium hypochlorite and mixed to form a second reaction medium. The second reaction medium exhibited no color indicating that the ammonia was not detected by the exemplary reagents of the present invention.

While the preferred methods of the present invention have been described above, other versions of the invention do exist. For example, the methodology described above can be employed to detect the presence of an amine in any aqueous sample of fluid, e.g., samples of taken from, for example, industrial fluids, natural water sources, as well as non-vaginal biological sources.

In addition, dyes can be manufactured by combining an amine, a developer reagent, a water-soluble base, and a halogen-containing oxidizing agent under the reaction conditions described above.

What is claimed is:

1. A method for screening for the presence of bacterial vaginosis, the method comprising the steps of:
   (a) combining a sample of vaginal fluid with a developer reagent selected from the group consisting of phenol, derivatives thereof, and mixtures thereof to form a first reaction medium;
   (b) combining the first reaction medium with a water soluble base and a halogen-containing oxidizing agent to form a second reaction medium having a pH of at least about 9.5;
   (c) observing the color of the second reaction medium, where the concentration of the halogen-containing oxidizing agent in the second reaction medium is about 0.12 or greater, on a molar basis, than the concentration of the developer reagent in the second reaction medium.

2. The method of claim 1 where at least a portion of steps (a) and (b) are performed sequentially.

3. The method of claim 1 where at least a portion of steps (a) and (b) are performed simultaneously.

4. The method of claim 1 where the developer reagent is selected from the group consisting of phenol, 2-phenylphenol, 3-phenylphenol, 4-phenylphenol, the alkali metal salts thereof, and mixtures thereof.

5. The method of claim 1 where the developer reagent comprises phenol.

6. The method of claim 1 where the amine selected from the group consisting of monoamines, diamines, homologues thereof, analogues thereof, and mixtures thereof.

7. The method of claim 1 where the amine selected from the group consisting of methylamine, isobutylamine, putrescine, cadaverine, histamine, tyramine, phenylethylamine, and mixtures thereof.

8. The method of claim 1 where the water soluble base comprises an alkali metal salt.

9. The method of claim 1 where the water soluble base is selected from the group consisting of alkali metal hydroxides, alkali metal carbonates, trialkali metal phosphates, and mixtures thereof.

10. The method of claim 1 where the water soluble base is selected from the group consisting of sodium hydroxide, potassium hydroxide, sodium carbonate, potassium carbonate, trisodium phosphate, tripotassium phosphate, and mixtures thereof.

11. The method of claim 1 where the water soluble base is selected from the group consisting of sodium hydroxide, potassium hydroxide, and mixtures thereof.

12. The method of claim 1 where the halogen-containing oxidizing agent is selected from the group consisting of chlorine-, bromine-, and iodine-containing oxidizing agents.

13. The method of claim 1 where the halogen-containing oxidizing agent comprises a chlorine-containing oxidizing agent.

14. The method of claim 1 where the halogen-containing oxidizing agent is selected from the group consisting of sodium hypochlorite, trichloroisocyanuric acid, 1-bromo-3-chloro-5-dimethylhydantoin, and mixtures thereof.

15. The method of claim 1 where the halogen-containing oxidizing agent comprises sodium hypochlorite.

16. The method of claim 1 where the pH of the second reaction medium is at least about 10.

17. The method of claim 1 where the pH of the second reaction medium is at least about 10.5.

18. The method of claim 1 where the pH of the second reaction medium is at least about 11.

19. The method of claim 1 where the pH of the second reaction medium is at least about 11.5.

20. The method of claim 1 where the pH of the second reaction medium is at least about 12.

21. The method of claim 1 where the pH of the second reaction medium is at least about 12.25.

22. The method of claim 1 where the pH of the second reaction medium is at least about 12.5.

23. The method of claim 1 where the pH of the second reaction medium is at least about 12.75.

24. The method of claim 1 where concentration of the halogen-containing oxidizing agent in the second reaction medium is about 0.14 or greater, on a molar basis, than the concentration of the developer reagent in the second reaction medium.

25. The method of claim 1 where concentration of the halogen-containing oxidizing agent in the second reaction medium is about 0.16 or greater, on a molar basis, than the concentration of the developer reagent in the second reaction medium.

26. The method of claim 1 where concentration of the halogen-containing oxidizing agent in the second reaction medium is about 0.18 or greater, on a molar basis, than the concentration of the developer reagent in the second reaction medium.

27. The method of claim 1 where concentration of the halogen-containing oxidizing agent in the second reaction medium is about 0.20 or greater, on a molar basis, than the concentration of the developer reagent in the second reaction medium.

28. The method of claim 1 where concentration of the halogen-containing oxidizing agent in the second reaction medium is about 0.21 or greater, on a molar basis, than the concentration of the developer reagent in the second reaction medium.

29. The method of claim 1 where concentration of the halogen-containing oxidizing agent in the second reaction medium is about 0.22 or greater, on a molar basis, than the concentration of the developer reagent in the second reaction medium.

30. The method of claim 1 where concentration of the halogen-containing oxidizing agent in the second reaction medium is 0.12 to about 1 times the concentration of the developer reagent in the second reaction medium, on a molar basis.

31. The method of claim 1 where concentration of the halogen-containing oxidizing agent in the second reaction medium is 0.14 to about 0.8 times the concentration of the developer reagent in the second reaction medium, on a molar basis.

32. The method of claim 1 where concentration of the halogen-containing oxidizing agent in the second reaction medium is 0.16 to about 0.6 times the concentration of the developer reagent in the second reaction medium, on a molar basis.

33. The method of claim 1 where concentration of the halogen-containing oxidizing agent in the second reaction medium is 0.18 to about 0.4 times the concentration of the developer reagent in the second reaction medium, on a molar basis.

34. The method of claim 1 where concentration of the halogen-containing oxidizing agent in the second reaction medium is 0.19 to about 0.3 times the concentration of the developer reagent in the second reaction medium, on a molar basis.

35. The method of claim 1 where the vaginal fluid comprises a viable pathogenic substance selected from the group consisting of bacteria, fungi, viruses, and mixtures thereof and where the second reaction medium is substantially free of any viable pathogenic substance.

36. A method for detecting the presence of an amine in a sample of fluid, the method comprising the steps of:
  (a) combining the sample of fluid with a developer reagent selected from the group consisting of phenol, derivatives thereof, and mixtures thereof and an amine to form a first reaction medium;
  (b) combining the first reaction medium with a water soluble base and a halogen-containing oxidizing agent to form a second reaction medium having a pH of at least about 9.5;
  (c) observing the color of the second reaction medium, where the concentration of the halogen-containing oxidizing agent in the second reaction medium is about 0.12 or greater, on a molar basis, than the concentration of the developer reagent in the second reaction medium.

37. The method of claim 36 where the fluid is a biological specimen.

38. A diagnostic kit comprising:
  (a) a developer reagent selected from the group consisting of phenol, derivatives thereof, and mixtures thereof;
  (b) water soluble base; and
  (c) a halogen-containing oxidizing agent,
where (i) the concentration of the halogen-containing oxidizing agent in a reaction medium formed by combining the developer reagent, the water soluble base, and the halogen-containing oxidizing agent is about 0.12 or greater, on a molar basis, than the concentration of the developer reagent in the reaction medium and (ii) the pH of the reaction medium is at least about 9.5.

39. A method for synthesizing 2,6-dichloroindophenol or a salt thereof, the method comprising the steps of:
  (a) reacting a phenol with an amine to form a first reaction medium; and
  (b) combining the first reaction medium with a halogen-containing oxidizing agent and a water soluble dye to form a second reaction medium, where step (b) is conducted under reaction conditions such that the second reaction medium comprises 2,6-dichloroindophenol or a salt thereof.

40. A method for synthesizing a dye, the method comprising the steps of:
  (a) reacting a phenol derivative selected from the group consisting of 2-phenylphenol, 3-phenylphenol, 4-phenylphenol, the alkali metal salts thereof, and mixtures thereof with an amine to form a first reaction medium; and
  (b) combining the first reaction medium with a halogen-containing oxidizing agent and a water soluble base to form a second reaction medium, where step (b) is conducted under reaction conditions such that the second reaction medium comprises the dye.

41. The dye formed by the method of claim 40.

42. The dye formed by the method of claim 40 where the phenol derivative comprises 2-phenylphenol and the dye is green.

43. A method for preparing a dye comprising the steps of:
  (a) reacting a developer reagent selected from the group consisting of phenol, 2-phenylphenol, 3-phenylphenol, 4-phenylphenol, the alkali metal salts thereof, and mixtures thereof with an amine selected from the group consisting of methylamine, isobutylamine, putrescine, cadaverine, histamine, tyramine, phenylethylamine, and mixtures thereof to form a first reaction medium; and
  (b) combining the first reaction medium with an alkali metal salt selected from the group consisting of sodium hydroxide, potassium hydroxide, sodium carbonate, potassium carbonate, trisodium phosphate, tripotassium phosphate, and mixtures thereof and an oxidizing agent selected from the group consisting of sodium hypochlorite, trichloroisocyanuric acid, and mixtures thereof to form a second reaction medium in which the dye is formed,
where the concentration of the oxidizing agent in the second reaction medium is about 0.12 or greater, on a molar basis, than the concentration of the developer reagent in the second reaction medium and the pH of the second reaction medium is at least about 9.5.

44. The method of claim 43 where the dye comprises a 2,6-dichloroindophenol salt.

45. The method of claim 43 where the dye prepared in accordance with the method is not indophenol.

46. A method for preparing a dye comprising the steps of:
  (a) reacting a developer reagent selected from the group consisting of phenol, derivatives thereof, and mixtures thereof with an amine to form a first reaction medium; and
  (b) combining the first reaction medium with a water soluble base and an halogen-containing oxidizing agent to form a second reaction medium having a pH of at least about 9.5 and comprising the dye,
where the concentration of the oxidizing agent in the second reaction medium is about 0.12 or greater, on a molar basis, than the concentration of the developer reagent in the second reaction medium.

47. A method for screening for the presence of bacterial vaginosis, the method comprising the steps of:
(a) combining a sample of vaginal fluid simultaneously or in any desired order with (i) a developer reagent selected from the group consisting of phenol, derivatives thereof, and mixtures thereof, (ii) a water soluble base, and (iii) a halogen-containing oxidizing agent to form a reaction medium having a pH of at least about 9.5;
(b) observing the color of the reaction medium, where the concentration of the halogen-containing oxidizing agent in the reaction medium is about 0.12 or greater, on a molar basis, than the concentration of the developer reagent in the reaction medium.

* * * * *